United States Patent
Bueno (10) Patent No.: US 7,452,877 B2
(45) Date of Patent: Nov. 18, 2008

(54) METHODS FOR TREATING DIGESTIVE FUNCTIONAL PATHOLOGIES

(75) Inventor: Lionel Bueno, Aussonne (FR)

(73) Assignee: Rytek, Saint Genies des Mourgues (FR)

(*) Notice: Subject to any disclaimer, the term of this patent is extended or adjusted under 35 U.S.C. 154(b) by 0 days.

(21) Appl. No.: 10/504,087

(22) PCT Filed: Mar. 14, 2003

(86) PCT No.: PCT/FR03/00831

§ 371 (c)(1),
(2), (4) Date: Oct. 21, 2004

(87) PCT Pub. No.: WO03/077893

PCT Pub. Date: Sep. 25, 2003

(65) Prior Publication Data

US 2005/0054577 A1    Mar. 10, 2005

(30) Foreign Application Priority Data

Mar. 15, 2002 (FR) .................... 02 03207
Sep. 6, 2002 (FR) .................... 02 11080

(51) Int. Cl.
*A61K 31/551* (2006.01)
(52) U.S. Cl. .................... 514/218
(58) Field of Classification Search ........... None
See application file for complete search history.

(56) References Cited

U.S. PATENT DOCUMENTS

| 6,248,549 B1 * | 6/2001 | Van Eyk et al. ........... 435/15 |
| 6,696,480 B2 * | 2/2004 | Liao ........... 514/411 |
| 2002/0045564 A1 * | 4/2002 | Van Eyk et al. ........... 514/1 |

FOREIGN PATENT DOCUMENTS

| EP | 0 797 992 | 10/1997 |
| RU | 2 148 997 | 5/2000 |
| WO | WO 98/14186 | 4/1998 |
| WO | WO 98/37096 | 8/1998 |
| WO | WO 99/14242 | 3/1999 |
| WO | WO 00/03746 | 1/2000 |
| WO | WO 00/07609 | 2/2000 |
| WO | WO 02/058687 | 8/2000 |
| WO | WO 00/57727 | 10/2000 |
| WO | WO 02/14499 | 2/2002 |

OTHER PUBLICATIONS

Bradesi et al., Neurogastroenterol. Mot. (Feb. 2002) 14(1), 75-82.*
Toulouse et al., British Journal of Pharmacology (2000) 129(1), 193-199.*
Turner et al, "Physiological Regulation of Epithelial Tight Junctions Is Associated With Myosin Light-chain Phosphorylation", American Journal of Physiology, American Physiological Society, Bethesda, MD, US, vol. 273, No. 4, Part 1, Oct. 1997, pp. C1378-C1385.

(Continued)

*Primary Examiner*—Phyllis G. Spivack
(74) *Attorney, Agent, or Firm*—Nixon & Vanderhye P.C.

(57) ABSTRACT

Methods are disclosed for treating hyperalgesia associated with irritable bowel syndrome comprising administering a direct and selective inhibitor of MLCK.

4 Claims, 12 Drawing Sheets

* $p<0.05$ significantly different from controls

OTHER PUBLICATIONS

Ma et al, "Ethanol Modulation of Intestin Epithelial Tight Junction Barrier", American Journal of Physiology, American Physiological Society, Bethesda MD, US, vol. 276, No. 4, Part1, Apr. 1999, pp. G965-G974.

Heyman et al, "Cytokine-Induced Alteration of the Epithelial Barrier to Food Antigens in Disease", Annals of The New York Academy of Sciences, New York Academy of Sciences, New York, NY, US, vol. 915, 2000, pp. 304-311.

Gassler et al, "Inflammatory Bowel Disease is Associated with Changes of Enterocytic Junctions", American Journal of Physiology: Gastrointestinal and Liver Physiology, American Physiological Society, US, vol. 281, No. 1, Jul. 2001, pp. G216-G228.

Kucharzik et al, "Neutrophil Transmigration in Inflammatory Bowel Disease is Associated with Differential Expression of Epithelial Intercellular Junction Proteins", American Journal of Pathology, Philadelphia, PA, US, vol. 159, No. 6, Dec. 2001, pp. 2001-2009.

Database Medline, US National Library of Medicine (NLM), Bethesda, MD, US; Feb. 2002, Cho So Yean et al, "Enhancement of paracellular transport of heparin disaccharide across Caco-2 cell monolayers", & Archives of Pharmacal Research, Korea (South), Feb. 2002, vol. 25, No. 1, Feb. 2002, pp. 86-92.

Mi Won Son et al, "Protective Effect of Taurine on TNBS-Induced Inflammatory Bowel Disease in Rats", Archives of Pharmacal Research, Natl. Fisheries University, Pusan, KR, vol. 21, No. 5, Oct. 1998, pp. 531-536.

Simonovic et al, "Enteropathogenic *Escherichia coli* Dephosphorylates and Dissociates Eccludin from Intestinal Epithelial Tight Junctions", Cellular Microbiology, Blackwell Science, Oxford, GB, vol. 2, No. 4, Aug. 2000, pp. 305-315.

Simmons et al, "Bidirectional Sodium Ion Movement via the Paracellular and Transcellular Routes Across Short-Circuited Rabbit Ileum", Biochimica et Biophysica Acta, Amsterdam, NL, vol. 448, No. 3, 1976, pp. 426-450.

Fasano et al, "Zonula Occludens Toxin Modulates tight Junctions Through Protein Kinase C-Dependent Actin Reorganization, in Vitro", Journal of Clinical Investigation, New York, NY, US, vol. 96, Aug. 1, 1995, pp. 710-720.

Karayiannakis et al, "Expression of Catenins and E-Cadherin During Epithelial Restitution in Inflammatory Bowel Disease", Journal of Pathology, Chichester, Sussex, GB, vol. 185, No. 4, Aug. 1998, pp. 413-418.

Soderholm et al, "Augmented Increase in Tight Junction Permeability by Luminal Stimuli in the Non-Inflamed Ileum of Crohn's Disease", Gut, British Medical Association, London, GB, vol. 50, No. 3, Mar. 2002, pp. 307-313.

Perry et al, "Reduced Cadherin-Catenin Complex Expression in Celiac Disease Can Be Reproduced in Vitro by Cytokine Stimulation", Laboratory Investigation, United States and Canadian Academy of Pathology, Baltimore, US, vol. 79, No. 12, Dec. 1999, pp. 1489-1499.

Patent Abstracts of Japan vol. 1998, No. 01, Jan. 30, 1998 & JP 09 241177, Sep. 16, 1997.

Groot, "Correlation Between Electrophysiological Phenomena and Transport of Macromolecules in Intestinal Epithelium", Veterinary Quarterly, Kluwer, Dordrecht, NL, vol. 20, No. Suppl 3, Jun. 1998, pp. S45-S49.

Savkovic et al, "EPEC-Activated ERK1/2 Partcipate in Inflammatory Response BT Not Tight Junction Barrier Disruption", American Journal of Physiology: Gastrointestinal and Liver Physiology, American Physiological Society, US, vol. 281, No. 4, Oct. 2001, pp. G890-G898.

Fasano et al, "Zonulin, a newly discovered modulator of intestinal permeability, and its expression in coeliac disease", LANCET, XX, XX, vol. 355, No. 9214, Apr. 29, 2000, pp. 1518-1519.

Kiliaan et al, "Stress stimulates transepithelial macromolecular uptake in rat jejunum", American Journal of Physiology 1998 United States, vol. 275, No. 5, 38-5, 1998, pp. G1037-G1044.

Verhaeren et al, "The Effect of 2,4,6-Triaminopyrimidine on Increased Mucosal Permeability of Guinea-Pig Colonic Mucosa, Following Administration of 1,8-Dihydroxy-Anthraquinonem, Salicylic Acid and Dinitrophenol", Pharmaceutisch Weekblad Scientific Edition, Bohn, Scheltema and Holkema, Amsterdam, NL, vo. 3, No. 1, Feb. 20, 1981, pp. 815-819.

Database Biosis, Biosciences Information Service, Philadelphia, PA, US; 1990, Gato-Pecina et al, "Use of the Paracellular Way for the Intestinal Absorption of Sugars" & Revista Espanola De Fisiologia, vol. 46, No. 4, 1990, pp. 343-352.

Krejs et al, "Effect of Protonated 2,4,6-Triaminopyrimidine, a Tight Junction Blocker, on Intestinal Transport in Dog Ileum in Vivo", Gastroenterology, Saunders, Philadelphia, PA, U, vol. 72, No. 4, Part 1, 1977, pp. 685-691.

Kinugasa et al, "Clauding Regulate the Intestinal Barrier in Response to Immune Mediators", Gastroenterology, W.B. Saunders Company, Philadelphia, US, vol. 118, No. 6, Jun. 2000, pp. 1001-1011.

Pothoulakis, "Effects of Clostridium Difficile Toxins on Epithelial Cell Barrier", Annals of the New Academy of Sciences, New York Academy of Sciences, New York, NY, US, vol. 915, 2000, pp. 347-356.

Hollander, "Intestinal Permeability, Leaky Gut, and Intestinal Disorders", Current Gastroenterology Reports, Current Science, US, vol. 1, No. 5, Oct. 1999.

Perry et al, "Intestinal permeability in coeliac disease", LANCET, XX, XX, vol. 358, No. 9294, Nov. 17, 2001, pp. 1729-1730.

Perry et al, "Reduced Expression of Z0-1 and Gamma Catenin in the Small Intestinal Mucosa of Untreated Cellac Disease", Gastroenterology, W.B. Saunders Company, Philadelphia, US, vol. 118, No. 4, Apr. 2000, p. AGAA369.

Choon Jin Ooi et al, "Regulation of Tight Junction Proteins in Human Subjects with Inflammatory Bowel Disease" Gastroenterology, W.B. Saunders Company, Philadelphia, Us, Vol. 118, No. 4, Apr. 2000, pp. AGAA795.

Ma et al, "Cytochalasin B Modulation of Caco-2 Tight Junction Barrier: Role of Myosin Light Chain Kinase", American Journal of Physiology: Gastrointestinal and Liver Physiology, American Physiological Society, US, vol. 279, No. 5, Nov. 2000, pp. G875-G885.

Ma et al, "Mechanism of Extracellular Calcium Regulation of Intestinal Epithelial Tight Junction Permeability: Role of Cytoskeletal Involvement", Microscopy Research and Technique, Wiley-Liss, Chichester, GB, vol. 51, No. 2, Oct. 15, 2000, pp. 156-168.

Database Medline: US National Library of Medicine (NLM), Bethesda, MD, US; Jun. 2000 Mankertz et al, "Expression from the human occludin promoter is affected by tumor necrosis factor alpha and interferon gamma" & Journal of Cell Science, England, Jun. 2000, vol. 113, (Pt 11), Jun. 2000, pp. 2085-2090.

Banan et al, "Carbonylation and Disassembly of the F-Actin Cytoskeletin in Oxidant Induced Barrier Dysfunction and Its Prevention by Epidermal Growth Factor and Transforming Growth Factor Alpha in a Human Colonic Cell Line", Gut, British Medical Association, London, GB, vol. 46, No. 6, Jun. 2000, pp. 830-837.

Turner, "Putting on the Squeeze' on the tight Junction: Understanding Cytoskeletal Regulation", Seminars in Cell and Developmental Biology, Academic Press, GB, vol. 11, No. 4, Aug. 2000, pp. 301-308.

Walsh et al, "Hepatocyte Growth Factor Influences Tight Junctions Via Regulation of the Apical Perijunctional Actin Cytoskeleten", Gastroenterology, W.B. Saunders Company, Philadelphia, US, vol. 118, No. 4, Suppl 2PT, Apr. 2000, pp. AGA-A671.

Sims et al, "Inhibitors of Myosin Light Chain Kinase Modulate Tight Junctions In CACO-2 Cells", Journal of Physiology, XX, XX, vol. 493P, 1996, pp. 87P-88P.

Ferrier et al, "Stress-Induced Disruption of Colonic Epithelial Barrier: Role of Interferon-γ and Myosin Light Chain Kinase in Mice", Gastroenterology 2003; 125:795-804.

Cenac et al, "$PAR_2$ activation alters colonic paracellular permeability in mice via IFN-γ-dependent and -independent pathways", J. Physiol. 558.3 (2004), pp. 913-925.

Ait-Belgnaoui et al, "Acute Stress-induced hypersensitivity to colonic distension depends upon increase in paracellular permeabiltiy: role of myosin light chain kinase", Pain 113 (2005) 141-147.

Camilleri et al, "Intestinal Permeability and irritable bowel syndrome", Neurogastroenterology and Motility (2007), pp. 1-8.

Cenac et al, "Proteinase-Activated Receptor-2-Induced Colonic Inflammation in Mice: Possible Involvement of Afferent Neurons, Nitric Oxide, and Paracellular Permeability", The Journal of Immunology, 2003, 170:4296-4300.

Moriez et al, "Myosin Light Chain Kinase Is Involved in Lipopolysaccharide-Induced Disruption of Colonic Epithelial Barrier and Bacterial Translocation in Rats", American Journal of Pathology, vol. 167, No. 4, Oct. 2005, pp. 1071-1079.

* cited by examiner

Figure 1 p<0.05 significantly different from SLIGRL

* : Significantly different from control (Tris)

+: Significantly different from Stress + Tris

* Significantly different from control at p<0.05
+ Significantly different from stress + solvent at p<0.05

METHODS FOR TREATING DIGESTIVE FUNCTIONAL PATHOLOGIES

This application is the US national phase of international application PCT/FRO3/00831 filed 14 Mar. 2003 which designated the U.S. and claims benefit of FR 02/03207, dated 15 Mar. 2002 and FR 02/11080 dated 6 Sep. 2002, the entire content of which is hereby incorporated by reference.

The invention concerns compositions and methods for treating intestinal pathologies. The invention also concerns compositions and methods enabling the regulation of paracellular permeability of the intestinal epithelium. The compositions and methods of the invention are based in particular on the use of agents or conditions modulating the opening of tight junctions of the intestinal epithelium. The invention can be used for preventive or curative treatment of various pathologies, such as digestive functional disorders (DFD), more particularly functional bowel disorders (FBD), and particularly irritable bowel syndrome (IBS), hyperalgesia and other abdominal pain syndromes, etc., in mammals, particularly humans.

The intestinal epithelium is the site of very important exchanges between the external medium and the body. Such exchanges can take place either across the cells of the epithelium, or by parallel networks. For instance, water and electrolyte transport, or else absorption of small molecules (molecular weight generally less than approximately 1000 Da) by the gastric, intestinal or colon mucosa, take place by a transcellular route, through epithelial cells or enterocytes. On the other hand, the absorption of large molecules and the passage of antigens, toxins or immune cells occur principally by the paracellular route, at the level of "tight junctions" located between epithelial cells.

Epithelial tight junctions (TJ) are structures which link the cells lining mucosal epithelia (gastrointestinal tract, lungs). Said structures ensure and control paracellular transport across the epithelium, from the exterior to the submucosa, of various macromolecules (allergens, irritants, toxins, microorganisms). Said structures also enable the migration of immune cells (e.g., immunocytes) towards the exterior (digestive tube). Tight junctions are flexible structures composed of a complex assembly of transmembrane proteins (occludins, claudins) and cytoplasmic proteins (zona occludens proteins ZO-1, ZO-2, ZO-3, AF7 proteins, cingulin or 7H6, etc.), which are associated with components of the cytoskeleton (actin, myosin filaments, etc.).

Among digestive functional disorders, abdominal pain without defecation disorder can be distinguished from functional bowel disorders. Abdominal pain without defecation disorder can be caused by allergies or food intolerance and can occur in celiac disease, for example. Functional bowel disorders affect 15 to 20% of the population and present as dyspepsia and/or intestinal symptoms for which no organic cause has yet been identified and which require a specific treatment. Digestive functional disorders meeting the Rome criteria all share the common feature of postprandial abdominal pain, whether located in the upper (dyspepsia) or lower abdomen. One particular disorder affecting the lower abdomen is irritable bowel syndrome (IBS). The pain of functional bowel disorders is usually relieved by defecation.

The pathophysiology of digestive functional disorders (DFD) is poorly understood although recent clinical investigations have indicated that these patients have a lower pain perception threshold to distention (visceral hyperalgesia) resulting in a state of digestive hypersensitivity. This appears to be related firstly to a sensitization of parietal mechanoreceptors by pro-inflammatory mediators. Indeed, the existence of modifications of the structure or density of certain immune cells in the submucosa, particularly the colon, argues in favor of an altered immune equilibrium with the resident microflora. This digestive micro-inflammatory state promotes sensitization of primary afferent nerve endings which might in turn facilitate transmission of nociceptive messages to the brain.

Such process of intestinal sensitization to pain can be induced by factors such as stress, pathogens, allergens, enzymes like trypsin or tryptase for example, bile salts, xenobiotics, chemical molecules such as glycerol, TNBS or taurocholate for example and/or sequelae of infection or surgery. However, the mechanisms by which said factors are capable of triggering the sensitization phenomenon have not been clearly documented in vivo. When allergens, pathogens and/or chemical molecules for example are absorbed, they enter into contact with the intestinal epithelial wall which prevents them from entering the body and coming into contact with immune cells. However, for sensitization to develop, this means that some allergens, pathogens and/or chemical molecules must be capable of crossing this epithelium to interact with immune cells. The conditions under which this transfer is possible in vivo remain obscure. Thus, while some studies on cell cultures in vitro suggest a role of tight junctions in this process, there is no evidence of an in vivo role of tight junctions in the development of sensitization. Likewise, while Coremans et al. (Ital. J. Gastroenterol. 1991; (8) S 1: 39-40) suggest a link between intracolonic administration of bile salts, and abdominal pain in a subject with irritable bowel syndrome, no results are presented to demonstrate a correlation between tight junctions and a process of sensitization of the intestinal epithelium to pain.

While malabsorption of bile salts is observed in only a small proportion of individuals with irritable bowel syndrome, alterations of transepithelial permeability have been described in subjects who develop IBS secondary to gastroenteritis (Spiller et al., Gut 2000; 47: 804-11) but with no mention of modifications in paracellular permeability, which was not investigated.

Experimental studies have found a correlation between irritable bowel syndrome and an increased presence of microorganisms in the submucosa (AGA. 1999), just as a relationship has been observed between chronic intestinal inflammatory disorders or functional bowel disorders and changes in the degree of immune activation (inflammation) of the intestinal lumen. However, these preliminary findings have not been confirmed or have not given rise to novel therapeutic approaches.

The invention results from the demonstration of an in vivo role of tight junctions of the intestinal epithelium in the process of sensitization to pain. The opening of tight junctions in the colon epithelium by different molecules or by stress results in spontaneous hyperalgesia or hypersensitivity to distention (a characteristic feature of IBS). The results obtained by the inventors thus show for the first time and in a surprising manner that the opening of tight junctions induces a chronic delayed state of hyperalgesia. The invention also results from the development of novel therapeutic strategies for treating intestinal pathologies, based on modulating paracellular permeability of the intestinal epithelium. In particular, the invention proposes for the first time, a therapeutic approach to intestinal pathologies based on the use of compounds or conditions enabling control of the opening of tight junctions of the intestinal epithelium. Thus, said compounds or conditions allow modulation of the cytoskeletal tension of intestinal epithelial cells or direct regulation, preferably reduction, even blockage, of the opening of tight junctions of the intestinal epithelium. Said approach therefore makes it possible to control the opening and closing of intestinal epithelium tight junctions, without necessarily having recourse to de novo protein synthesis and/or important protein and/or structural degradations in the epithelium. Said strategy enables a regulation of intestinal epithelial permeability which is specific, fine and reactive, and hence an action on the transfer of allergens, pathogens and/or chemical molecules to immune cells. Said strategy is particularly adapted to obtaining a rapid biological effect which can be controlled over time (reversible).

In this regard, the results presented hereinbelow show that a substance capable of relaxing epithelial tight junctions (PAR-2 receptor activator peptides) triggers delayed hyperalgesia and hypersensitivity to distention. Similarly, intracolonic infusion of bile salts (taurocholate for example) increases the passage of macromolecules by opening tight junctions and is accompanied by the same delayed hyperalgesia state. Finally, constraint stress increases the permeability of tight junctions and results in a state of rectal hyperalgesia. The results presented in the examples further show that in all cases (PAR-2 activator peptide, taurocholate or stress), the inhibition of this increase in paracellular permeability by a chemical agent (TAP for example) which binds and blocks tight junctions, or by molecules which relax the epithelial cell cytoskeleton (ML-7, PD98059), prevents or reduces this hyperalgesia characteristic of DFD and particularly IBS.

Therefore, a first object of the invention is more particularly based on the use of a compound controlling the opening of tight junctions of the intestinal epithelium, for preparing a medicament for preventive or curative treatment of intestinal pathologies characterized by a state of hyperalgesia.

Another object of the invention is based on a method for preventive or curative treatment of intestinal pathologies characterized by a state of hyperalgesia, comprising administering to a subject an efficacious quantity of a compound controlling the opening of tight junctions of the intestinal epithelium.

In particular, the compounds controlling the opening of tight junctions of the intestinal epithelium are compounds which modulate cytoskeletal tension of intestinal epithelial cells or compounds which reduce, even block, the opening of tight junctions of the intestinal epithelium.

The invention is thus based on the use of compounds modulating the tension and state of contraction of the cytoskeleton of intestinal epithelial cells or preventing excessive opening of tight junctions which results in hyperalgesia or hypersensitivity to intestinal distention.

The proteins composing tight junctions are associated with the cytoskeleton of the cells they link together. The invention proposes that the tension of the cytoskeleton or the opening of tight junctions can be modulated in subjects with intestinal diseases or disorders so as to act in a non-destructive and transient manner on the permeability of their intestinal epithelium. So, cytoskeletal contraction should promote opening of tight junctions, while cytoskeletal relaxation (or inhibition of contraction) should promote closing of tight junctions. It is also possible to directly modulate tight junctions, in particular on the proteins of which they are composed, by reducing or blocking the opening thereof.

Preferably, then, the invention provides for the use of compounds (or conditions) that modulate the contraction of the cytoskeleton of intestinal epithelial cells (particularly human) or that directly control the opening of tight junctions of the intestinal epithelium (particularly human). Depending on the condition to be treated, compounds are used which inhibit cytoskeletal contraction of intestinal epithelial cells, or which activate or promote it, or compounds which directly reduce or block the opening of tight junctions or which increase the opening thereof.

The activity of the compound modulating the opening of tight junctions of the intestinal epithelium, particularly by modulating cytoskeletal tension, can be direct or indirect, that is to say, directed on the very components of the cytoskeleton, or on the regulators of cytoskeletal tension. Though not by way of limitation, preferred compounds are those acting directly on cytoskeletal tension. Moreover, compounds displaying selective activity on cytoskeletal tension are preferred, that is to say, typically, compounds which do not directly affect the structure of the proteins composing the tight junctions.

A compound is considered to modulate cytoskeletal tension when it modulates the opening of tight junctions. An inhibitory effect on the contraction or tension of actin and/or myosin filaments does not necessarily have to be complete or total, but should reduce cytoskeletal contraction or tension enough to reduce the opening of tight junctions.

Reduction of the opening of tight junctions preferably corresponds to a reduction of at least 25%, advantageously approximately 30%, even more preferably approximately 50% of the paracellular permeability of the intestinal epithelium. Paracellular permeability can be measured by means of a tracer such as $^{51}$Cr-EDTA which, after passage in the blood, is assayed in the urine over 24 hours (see example 1).

Different types of compounds may be used within the scope of the invention. For instance, in the spirit of the invention, the term "compound" must be understood in a broad sense, that is to say, as denoting any agent, substance, composition, condition, treatment or method enabling modulation of the opening of tight junctions of the intestinal epithelium. Advantageously, it is an agent (e.g., a molecule) or a combination or association of agents.

According to a first embodiment, compounds are used which directly modulate the opening of tight junctions, particularly by binding, preferably in a reversible manner, to the proteins composing tight junctions. A particular example is TAP (2,4,6-triaminopyrimidine).

According to another embodiment, one uses compounds which inhibit (or modulate) the contraction or tension of the myosin and/or actin light chain, or compounds which inhibit (or modulate) the degradation of actin.

Examples of such compounds include in particular inhibitors of myosin light chain kinase (MLCK). It should be pointed out that studies reported in the prior art apply more to the use of compounds designed to open intestinal tight junctions, in order to promote the passage of large molecules, whereas the present invention more preferably aims to exert an opposite action, intended to reduce the permeability of tight junctions.

A particular example of selective MLCK inhibitor is the compound ML-7 {1-(5-iodonaphthalene-1-sulfonyl)-1H-hexahydro-1,4-diazepine} (Makishima M. et al., FEBS Lett. 1991; 287: 175). Other particular examples of such inhibitors are the compound ML-9 (Wilson D P. et al., J Biol Chem. 2001; 13: 165) or other nonselective compounds: wortmannin (Warashina A., Life Sci. 2000; 13: 2587-93), H-7 (Piao Z f et al., Mol. Cell. Biol. Res. Commun. 2001; 4: 307-12) and KT 7692 (Warashina A., Life Sci. 2000; 13: 2587-93).

Other targets acting on cytoskeletal tension are in particular the myosin binding proteins, such as for example cingulin, or the junction molecules, such as cadherin-E, catenin-α or desmosomes. Modulation of the activity or expression of said proteins allows regulation of cytoskeletal tension, in the scope of the invention.

A particular object of the invention is therefore the use of a modulator (particularly an inhibitor) of the activity or structure or expression of cytoskeleton molecules. For example the compound may be an antisense nucleic acid, a synthetic molecule, an antibody fragment, among others.

According to another embodiment, it is possible to use compounds that inhibit the synthesis of proteins or other molecules ensuring the binding between the proteins of the cytoskeleton and the proteins of tight junctions. Among proteins of tight junctions, particular examples include the occluding, claudins, ZO-1, ZO-2, ZO-3, AF7 and 7H6. The invention discloses a means of modulating the opening or closing of tight junctions which is therefore based on regulating the synthesis of binding proteins between the cytoskeleton and the proteins of tight junctions. By stimulating said synthesis, the links between tight junctions and the cytoskeleton are expected to be strengthened, leading to lower permeability of the epithelium.

Other compounds that can be used in the invention are for example inhibitors of mitogen activated kinases (MAPKK), particularly MEK1 kinase or kinase-PI3, such as the compounds PD098,059 {2-(amino-3-methoxyphenyl)-4H-1-benzopyran-4-one} (Alessi et al., J. Biol. Chem. 1995; 270: 27589) or LY294002 {2-(4-morpholinyl)-8-phenyl-1(4H)-benzopyran-4-one} (Vlahos et al., J. Biol. Chem. 1994; 269: 5241).

Other molecules that can be used to indirectly regulate the tension of the cytoskeleton are the growth factors, such as hepatic growth factor (HGF), endothelial growth factor (EGF) or certain cytokines which can be released by immune cells, such as interleukins-1, -4, -13, or factors such as IGF-1 or interferon gamma.

Another approach by which to indirectly regulate cytoskeletal tension is based on the use of the GLP2 peptide ("glucagon-like peptide 2") or derivatives thereof, which can modify intestinal epithelial permeability by an indirect effect on cytoskeletal contraction. Likewise, some molecules acting on receptors located at the apical pole of epithelial cells (e.g., proteinase receptors, PAR-2) can act indirectly on the cytoskeleton.

A preferred embodiment of the invention comprises the use of agents acting directly on cytoskeletal tension, particularly molecules inhibiting cytoskeletal contraction, in particular molecules inhibiting the contraction or tension of myosin and/or actin light chains, or inhibiting actin degradation.

As indicated hereinabove, the compounds used are advantageously molecules, which may be alone or in combination, biological extracts, and the like. Said molecules may be synthetic, semisynthetic or biological, particularly of animal, viral, plant or bacterial origin.

The invention is useful for treating or managing pathologies or disorders of the digestive system characterized by a state of hyperalgesia, particularly functional bowel disorders, chronic intestinal inflammatory diseases (CIID), food intolerance (allergies, formulations, etc.) characterized by chronic abdominal pain. it is particularly adapted to the preventive or curative treatment of hyperalgesia and in particular irritable bowel syndrome (IBS) regardless of its type (constipation-predominant, diarrhea-predominant or a combination of the two), but also chronic abdominal pain that is not classified as IBS, such as functional abdominal pain without defecation disorder (FAPS functional abdominal pain syndrome) and pain related to food intolerance and celiac disease. It can be used preventively in subjects with a predisposition or sensitivity to this type of disorder, or as curative treatment, for example during acute episodes or over longer periods. The compositions and methods of the invention make it possible to alleviate the suffering of subjects, attenuate the symptoms or the cause of these disorders.

In fact, the invention shows in a surprising manner that suppressing the increase in paracellular permeability associated with opening of tight junctions prevents the development of abdominal hyperalgesia.

A particular object of the invention is based on the use of a compound such as defined hereinabove for preparing a medicament for controlling, particularly for reducing, the paracellular permeability of the intestinal epithelium in subjects with intestinal diseases characterized by a state of hyperalgesia, particularly chronic inflammatory diseases characterized by an accumulation of immunocytes (for example mast cells and/or enterochromaffin cells) in the submucosa, by a heightened sensitivity of parietal mechano-receptors and possibly by an infiltration of colonic bacteria into the submucosal layer, for example hyperalgesia and particularly irritable bowel syndrome.

Another particular object of the invention is based on the use of a compound such as defined hereinabove for preparing a medicament for reducing sensitization to allergens, pathogens and/or chemical molecules in subjects with or susceptible to intestinal functional disorders, particularly intestinal pathologies characterized by an accumulation of immunocytes, for example mast cells and/or enterochromaffin cells, in the submucosa, by a heightened sensitivity of parietal mechano-receptors and possibly by an infiltration of colonic bacteria into the submucosal layer, for example hyperalgesia and particularly irritable bowel syndrome.

Another particular object of the invention is based on the use of a compound such as defined hereinabove for preparing a medicament for reducing transepithelial migration of immunocytes and accumulation of immunocytes in the submucosal layer in subjects with an intestinal functional pathology, particularly an intestinal pathology causing abdominal hyperalgesia, for example irritable bowel syndrome, characterized by an accumulation in the submucosa of immunocytes, particularly mast cells and/or enterochromaffin cells, by a heightened sensitivity of parietal mechano-receptors and possibly by an infiltration of colonic bacteria into the submucosal layer.

The invention also relates to methods for treating the hereinabove conditions, comprising administering to a subject with an intestinal pathology or susceptible to intestinal pathologies, a compound or treatment such as defined hereinabove. Preferably, the compound or treatment is administered at a dose effective to reduce paracellular permeability of the intestinal epithelium and/or to reduce sensitivity to pain and/or to reduce transepithelial migration of allergens, toxins, irritants or microorganisms and resultant accumulation of immunocytes in the intestinal submucosa.

The compound may be administered by different routes and in different forms. For instance, the compound may be in liquid or solid form, typically in the form of a tablet, capsule, ampoule or oral solution, a solution for injection, etc. Compounds formulated for oral administration (oral solutions, tablets, ampoules, syrups, etc.) or for rectal administration are preferred. A suppository formulation is particularly preferred, where possible. Of course, other formulations are possible, such as injections (intraperitoneal, intradermal, subcutaneous, intramuscular, intravenous, intraarterial, etc.), pastes, gels, and the like.

The compounds may be used alone or in combination and/or in association with other active agents, such as for instance other active substances used in the treatment of irritable bowel syndrome. Examples are anticholinergic, prokinetic, antidiarrheal compounds, modifiers of intestinal motility, etc. These different agents may be used in combination therapy, and administered separately, in combination, spread out over time or concomitantly.

Another object of the invention is based on a pharmaceutical association or product comprising at least one compound modulating the opening of tight junctions of the intestinal epithelium and at least one other active agent selected in the group consisting of anticholinergic compounds, prokinetic substances, antidiarrheals, laxatives or modifiers of motility, abdominal sensitivity (or digestive sensitivity), in view of use in combination, separately or spread out over time.

Another object of the invention is a pharmaceutical composition comprising at least one compound modulating the opening of tight junctions of the intestinal epithelium and a pharmaceutically acceptable excipient, said composition preferably being formulated for oral or rectal administration. Preferably, the composition is in the form of a suppository or oral solution.

Other aspects and advantages of the invention will become apparent in the following examples, which are given for purposes of illustration and not by way of limitation.

LEGENDS OF FIGURES

CPI: Protein inhibitor of the phosphorylated state of myosin phosphatase.

MBS: Myosin binding subunit.

MP: Myosin phosphatase.

M20: 20 Kda subunit.

Cat: Catalytic subunit of myosin phosphatase.

GEFs: Guanine nucleotide exchange factors.

AA: Arachidonic acid.

Ins (1,4,5) $P_3$: Inositol (1,4,5) triphosphate.

PLC: Phospholipase C.

SR: Sarcoplasmic reticulum.

EXAMPLES

Example 1

Reduction of Rectal Hyperalgesia by a Blocker of Tight Junctions

The intestinal epithelium possesses structures linking epithelial cells which ensure controlled passage of immunocytes in the intestinal submucosa. This example shows that certain molecules known to increase intestinal paracellular permeability such as SLIGRL promote the accumulation of immunocytes in the intestinal submucosa (mast cells, enterochromaffin cells) and that this effect can be prevented (e.g., inhibited, reduced) by intracolonic administration of a blocker of tight junctions.

Figure 1:
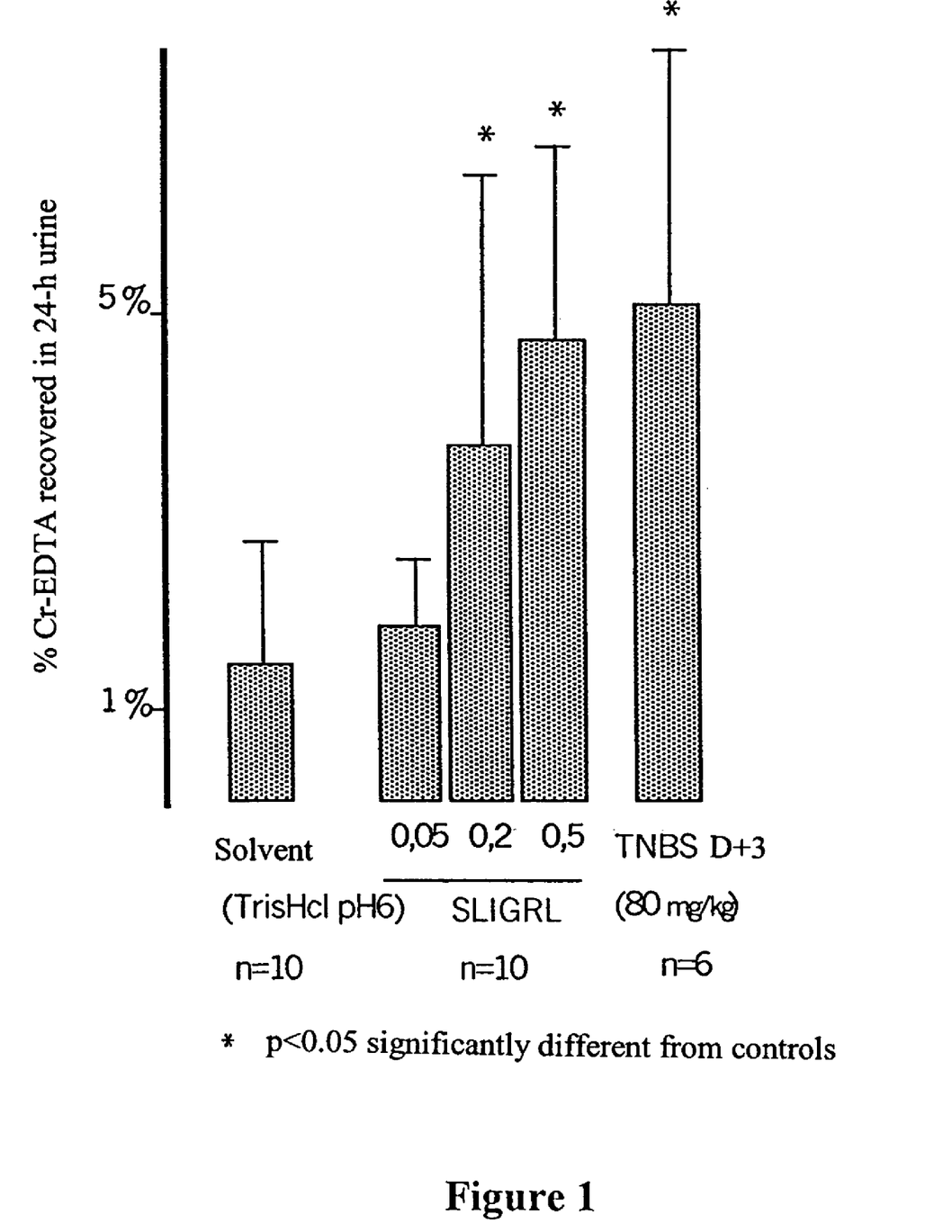
FIG. 1: Effect of increasing doses of a PAR-2 receptor activator peptide (SLIGRL) on absorption of a macromolecule ($^{51}$Cr-EDTA) expressed as percentage recovery in the 24-hour urine of rats.
Figure 2:
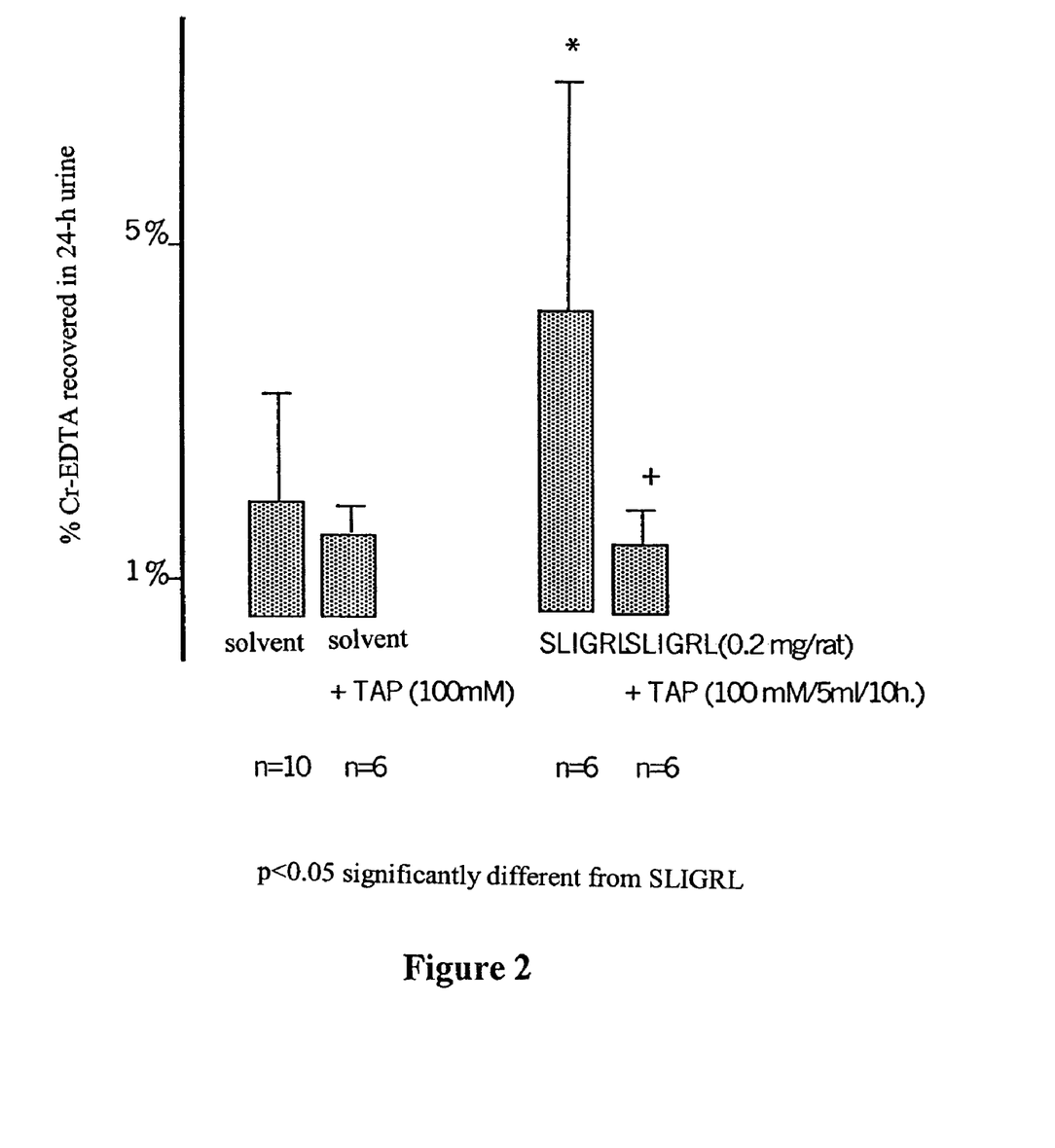
FIG. 2: Effect of concomitant administration of a tight junction blocker (TAP-100 mM) on the increase in paracellular permeability to $^{51}$Cr-EDTA induced by intracolonic injection of SLIGRL (0.5 mg/rat). This increase was abolished by 10-h infusion of 2,4,6-triaminopyrimidine (TAP) which blocks tight junctions (TJ).
Figure 3:
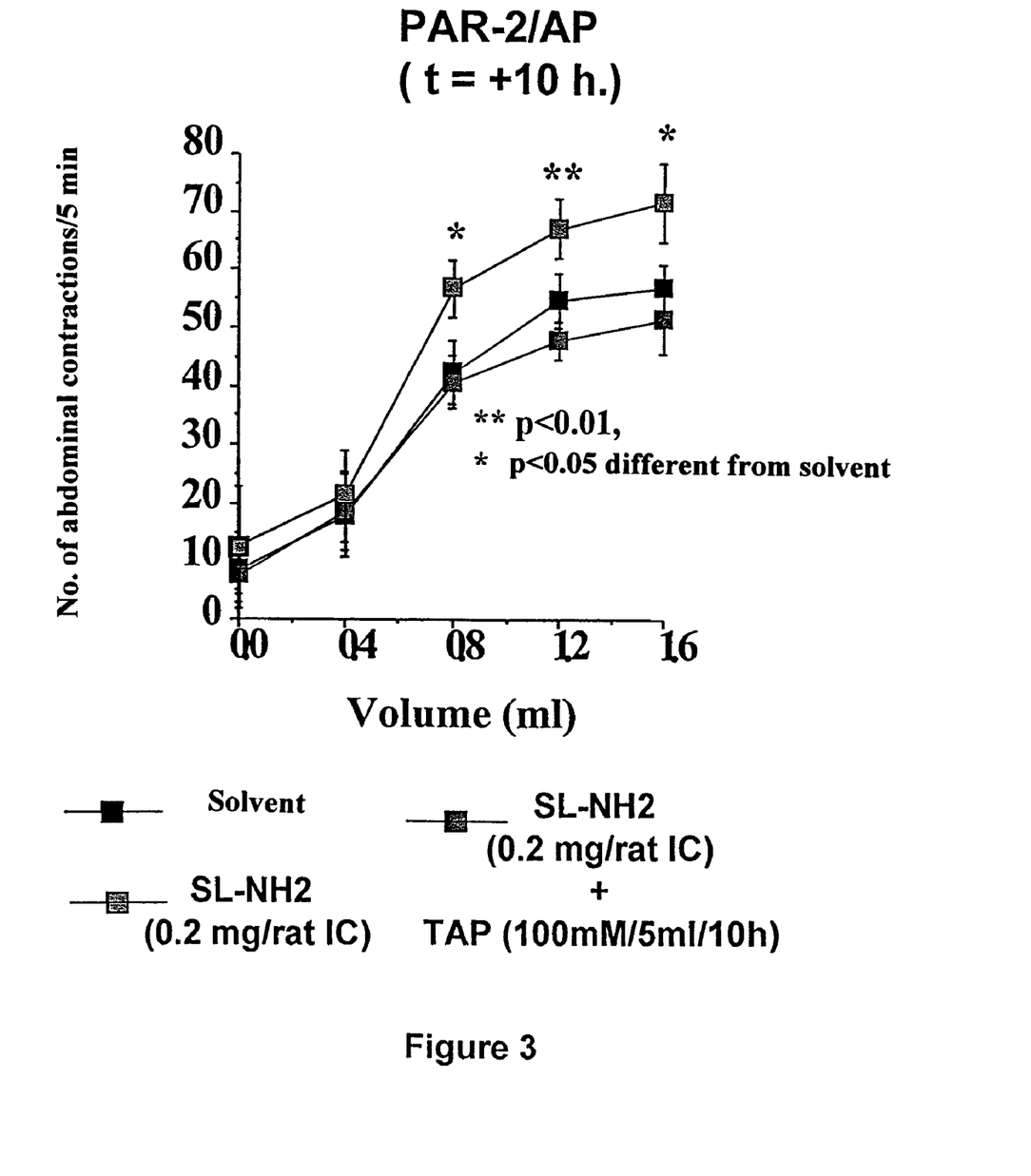
FIG. 3: Suppression by a TJ blocker (TAP-100 mM), of rectal hypersensitivity to distention induced by SLIGRL (0.2 mg).

Six groups of eight male Wistar rats (200-250 g) were used for this study. Animals received an indwelling intracolonic catheter in the proximal colon (3 cm from the caeco-colic junction). During these studies, four groups of rats received a 10-hour intracolonic infusion of $^{51}$Cr-EDTA solution (0.5 µC/h). Animals were placed in individual cages and total 24-hour urine was collected. Radioactivity was measured to evaluate the permeability of the colon mucosa to $^{51}$Cr-EDTA. Increasing doses of a PAR-2 activator peptide (SLIGRL) were injected in the colon lumen (groups 2, 3 and 4) at time t=0 (start of $^{51}$Cr-EDTA infusion) at a dose of 0.05, 0.2 and 0.5 mg/rat. Group 1 received the solvent. FIG. 1 illustrates the dose-dependent increase in permeability to $^{51}$Cr-EDTA induced by SLIGRL demonstrating its ability to increase paracellular permeability.

Exemple 2

Reduction of Rectal Hyperalgesia by TAP

Female rats subjected to a constraint stress for two hours develop rectal hypersensitivity to distention. It is also known that such constraint stress increases colon permeability to macromolecules (paracellular permeability).

This study was carried out on three groups of eight female Wistar rats (225-250 g) fitted with electrodes implanted in abdominal striated muscle so as to record abdominal contractions. Animals also received intracolonic catheters. At time t=0, animals were subjected to a constraint stress of 2 hours during which they also received intracolonic infusion of either solvent (Tris—group 1) or TAP (100 mM, group 2) or Tris with fictive stress (group 3).

Figure 4:
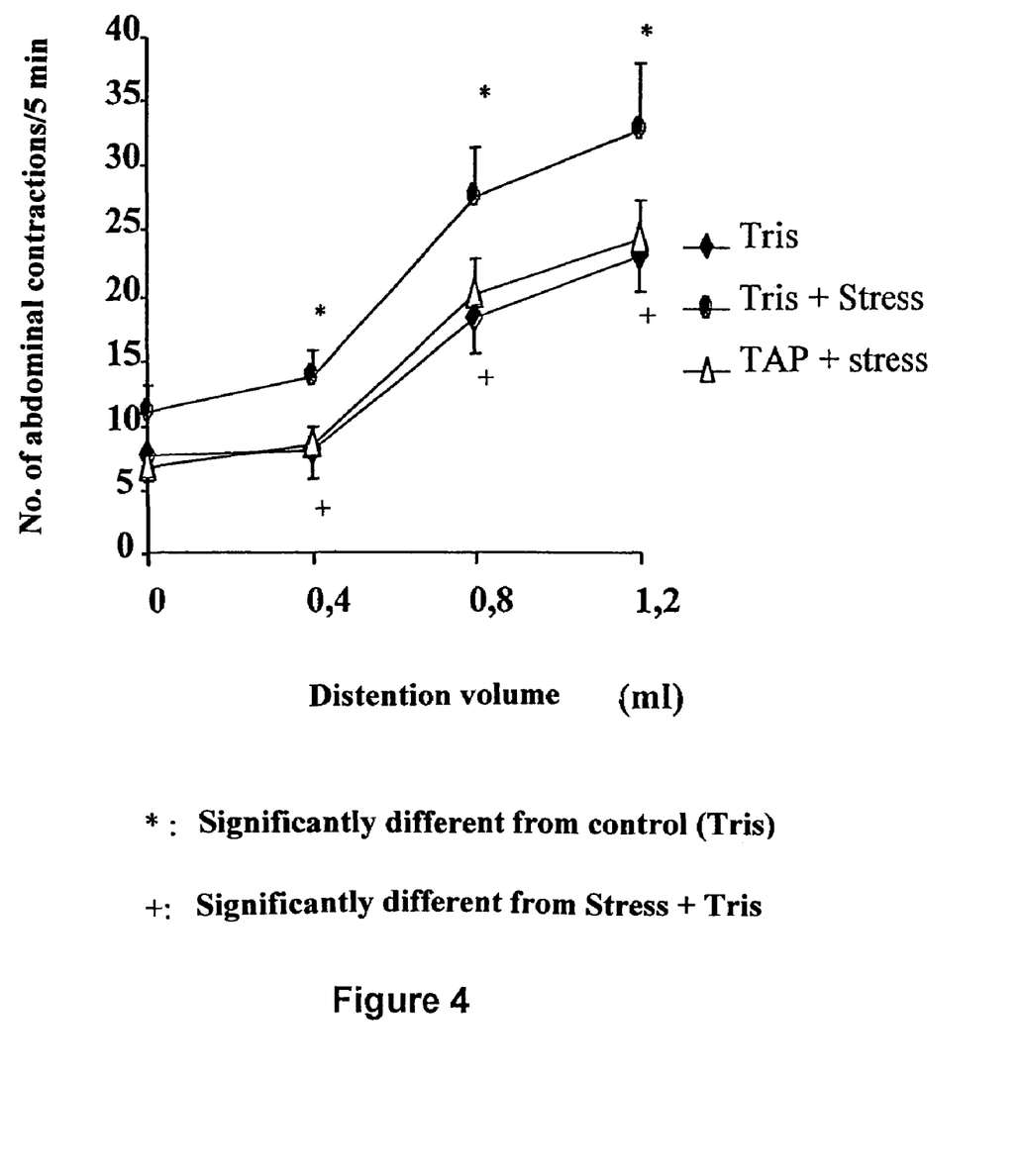
FIG. 4: Effect of intracolonic infusion of a TJ blocker on rectal hyperalgesia to distention induced by constraint stress in female rats.

The results show that constraint stress (stress) significantly increased the number of abdominal contractions (hyperalgesia) at all distention volumes (0.4, 0.6 and 1.2 ml) and that this effect was abolished by concomitant intracolonic infusion of TAP (FIG. 4).

Example 3

Reduction of Rectal Hyperalgesia by ML-7

Figure 5:
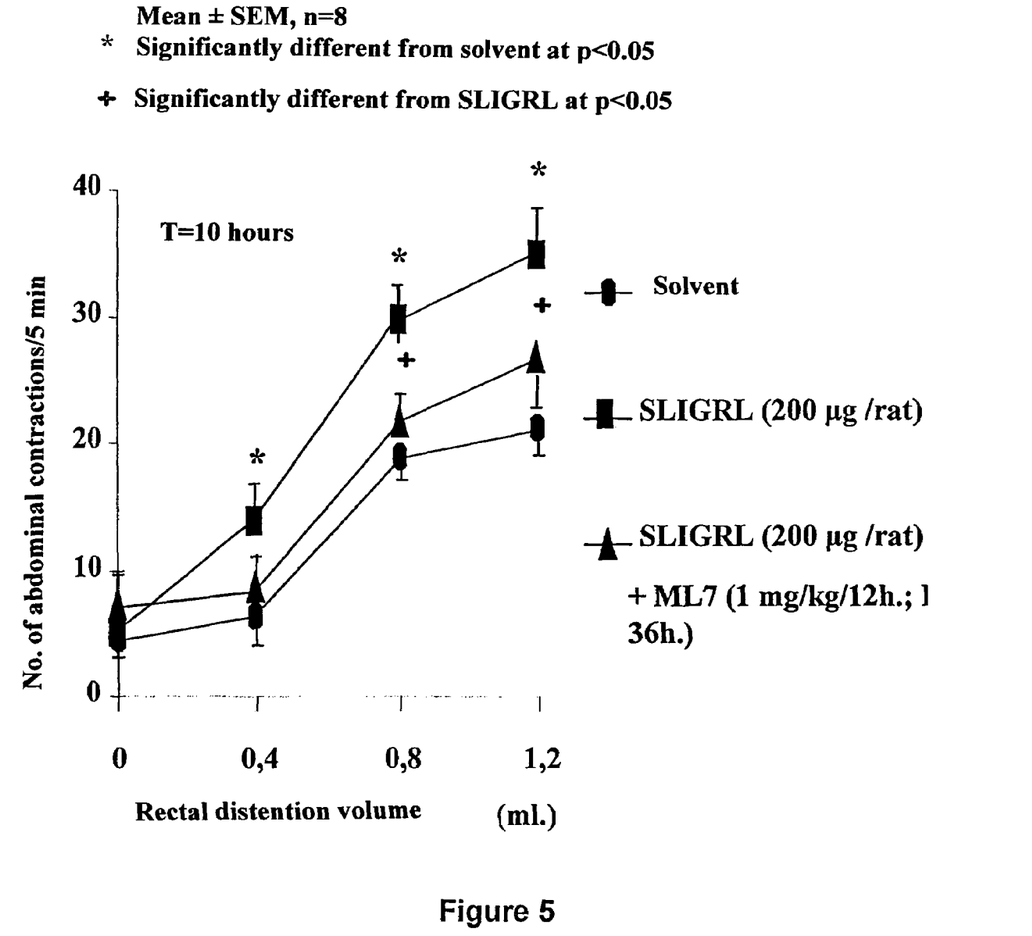
FIG. 5: Effects of repeated administration of an MLCK inhibitor on rectal hyperalgesia induced by intracolonic administration of SLIGRL (200 µg) in rats. With regard to SLIGRL-induced hyperalgesia, only repeated administration of ML-7 (three doses of 1 mg/kg at 12 h intervals) reduced hyperalgesia for all distention volumes.
Figure 7:
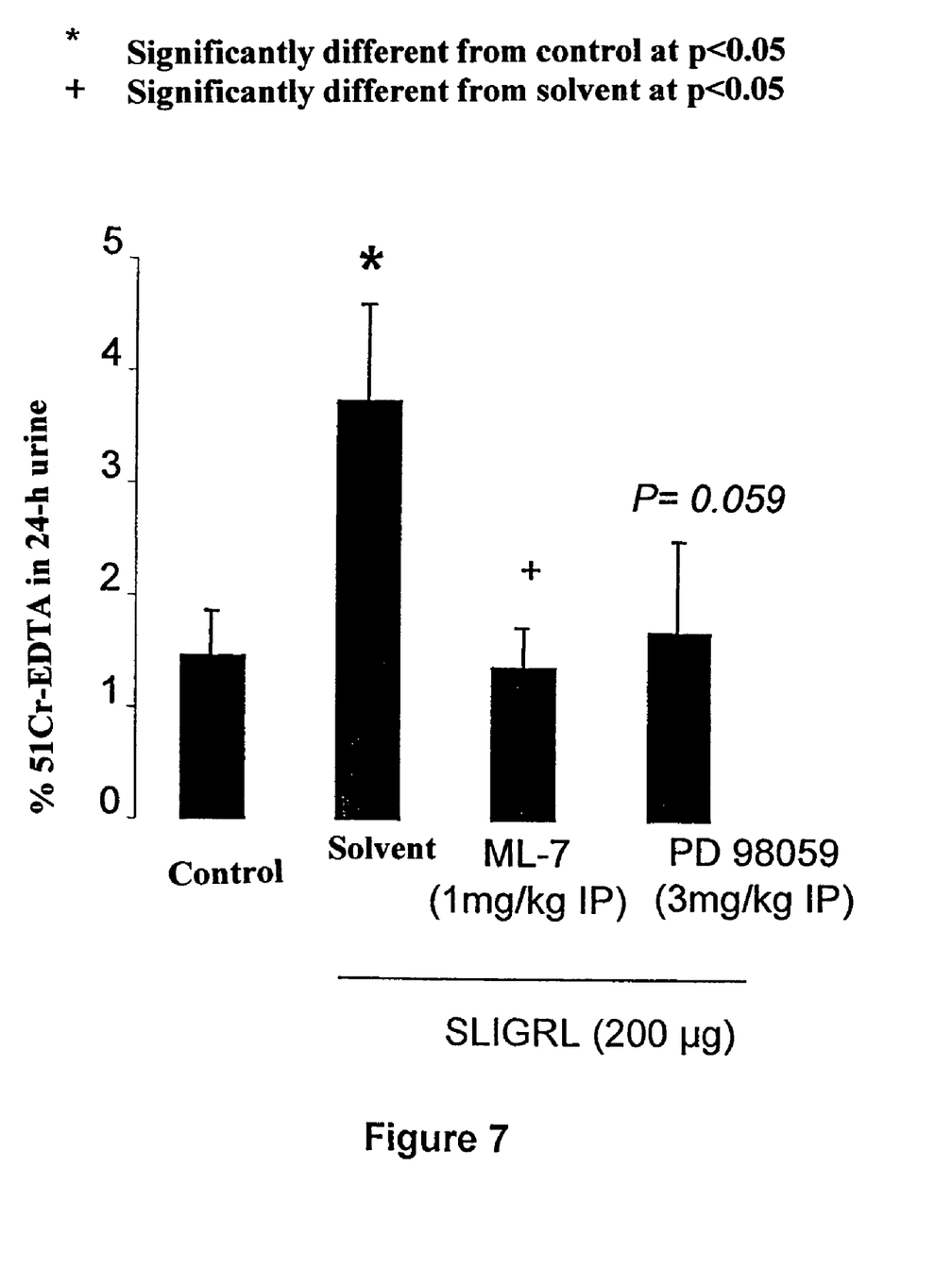
FIG. 7: Comparative effects of ML-7 and PD 98059 on the increase in epithelial tight junction permeability induced by a PAR-2 receptor activator (SLIGRL) in rats. Measurements of colon permeability according to the method and conditions described in example 1, on six groups of rats, showed that at doses which reduced abdominal pain, the direct MLCK inhibitor (ML-7) and indirect inhibitor (PD 98059) suppressed the increase in tight junction permeability induced by SLIGRL.
Figure 8:
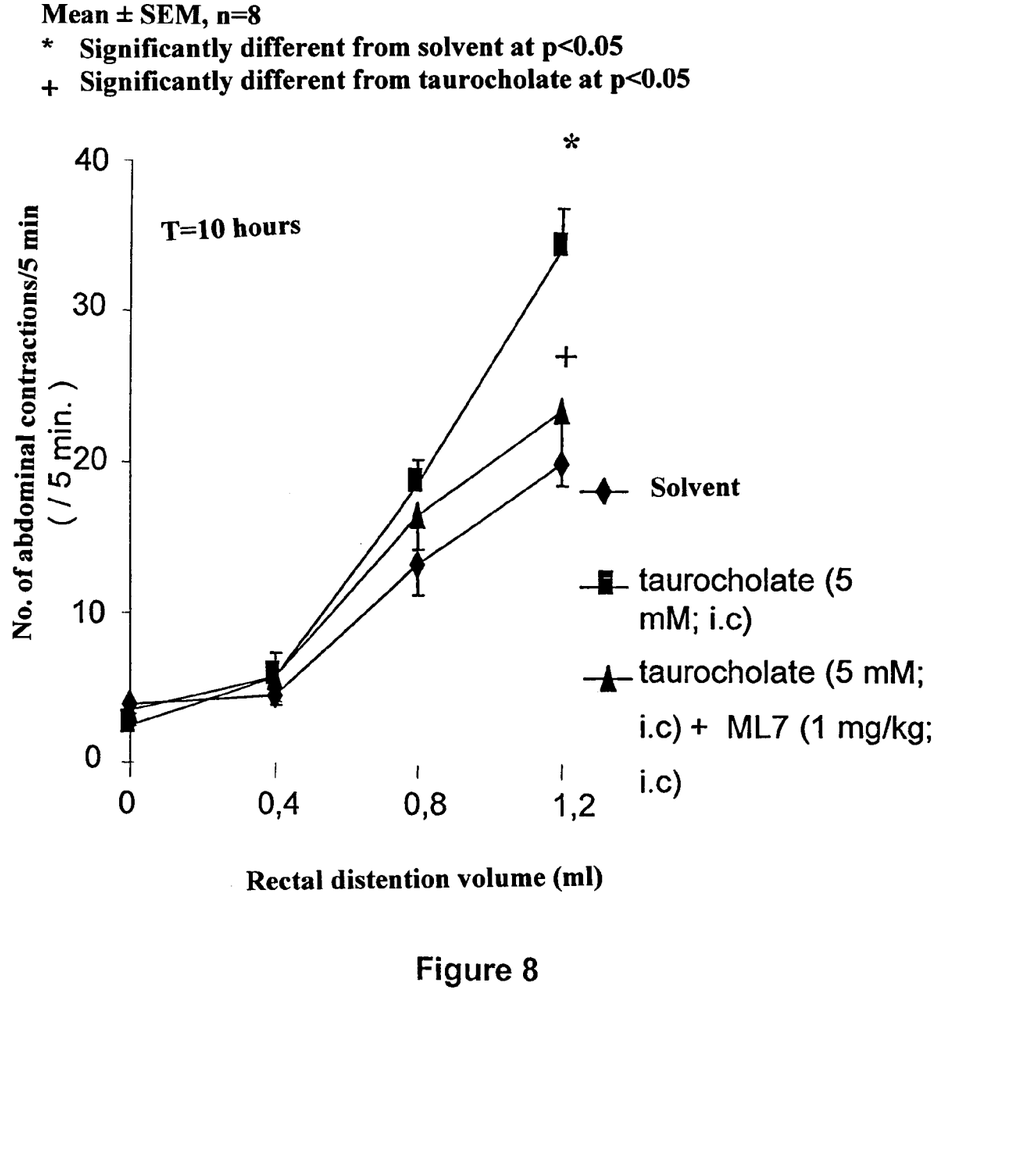
FIG. 8: Effect of a single administration of an MLCK inhibitor (ML-7) on the increase in the nociceptive response induced by intracolonic administration of taurocholate in rats.
Figure 9:
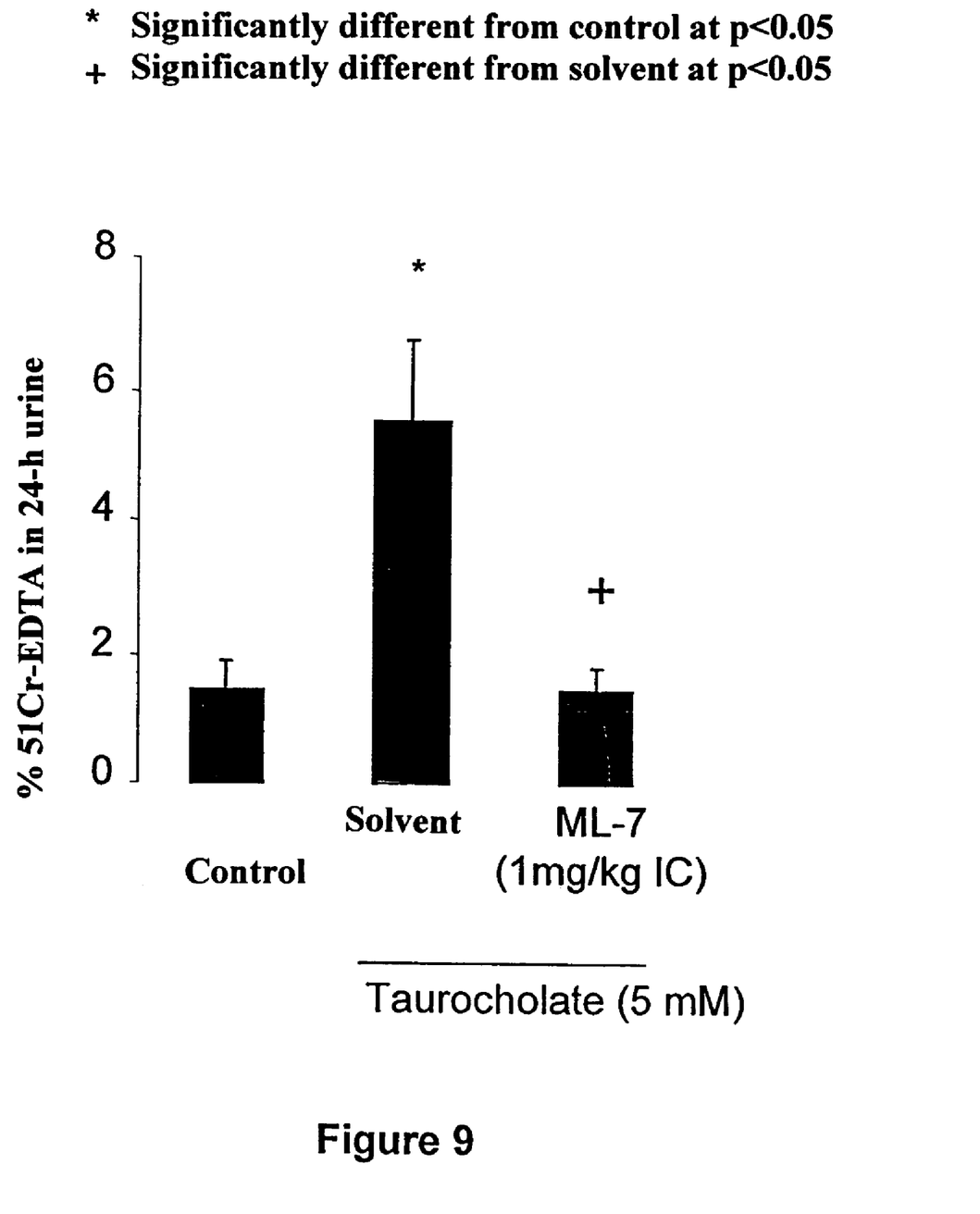
FIG. 9: Effect of ML-7 on the increase in epithelial tight junction permeability induced by taurocholate in rats. Measurements of colon permeability according to the method and conditions described in example 1, on six groups of rats, showed that at doses which reduced abdominal pain, ML-7 (direct MLCK inhibitor) suppressed the increase in tight junction permeability induced by taurocholate.
Figure 10:
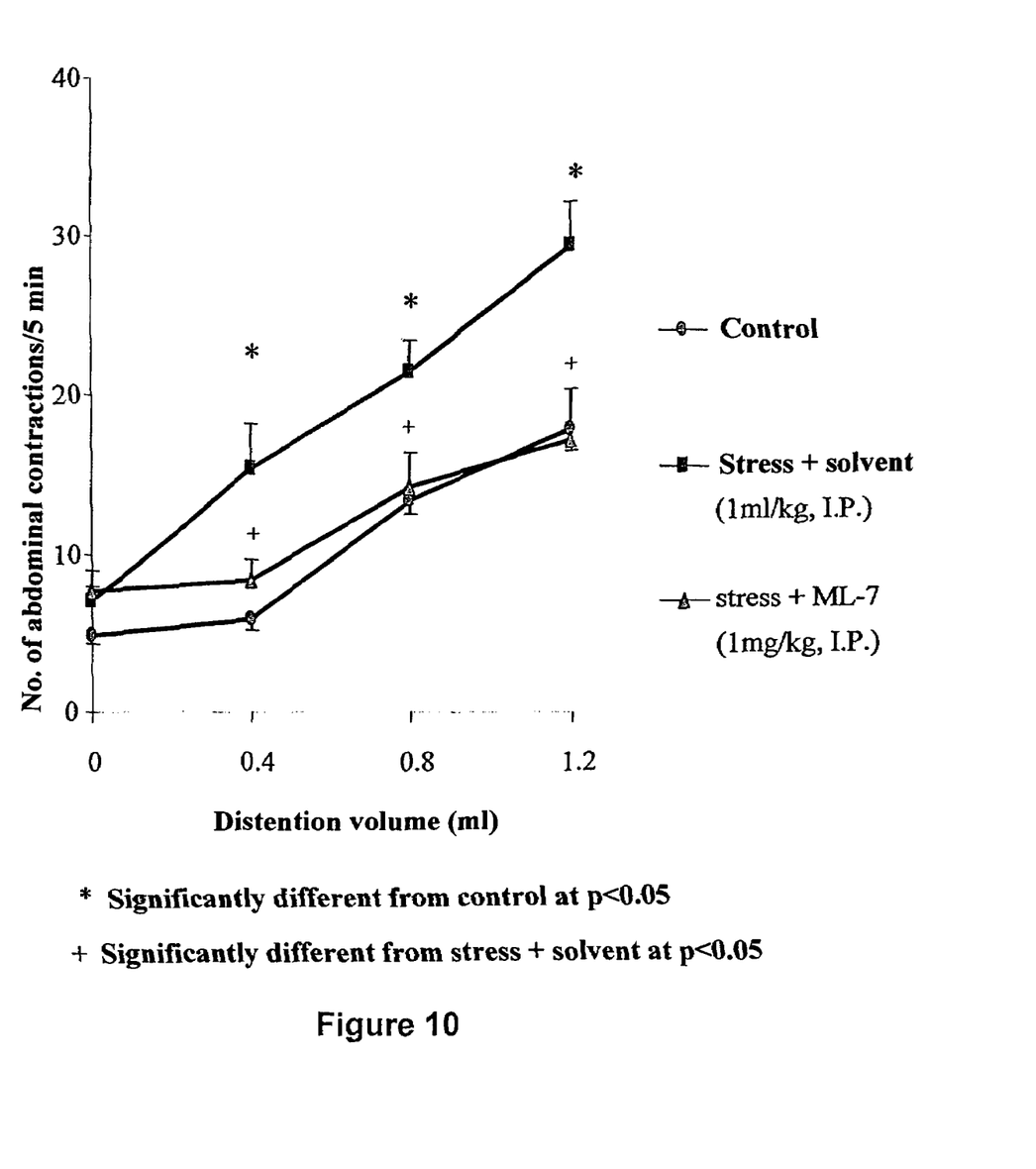
FIG. 10: Effect of an inhibitor of cytoskeletal contraction of colon epithelial cells acting on MLCK (ML-7) on colon hypersensitivity to distention induced by constraint stress in rats (mean±SEM, n=8).

The protocol described in example 1 was used on 3×3 groups of 7-8 rats given intracolonic infusion of SLIGRL (200 µg) or taurocholate (5 mM) but previously treated with ML-7 (MLCK inhibitor) by the intramuscular route. The results in FIGS. 8 and 9 show that a single treatment with ML-7 at a dose of 1 mg/kg reduced hyperalgesia induced by intracolonic administration of taurocholate. The results in FIGS. 5 and 7 show that a single treatment with ML-7 at a dose of 1 mg/kg reduced hyperalgesia induced by intracolonic administration of SLIGRL.

Example 4

Reduction of Rectal Hyperalgesia by PD 98059

Figure 6:
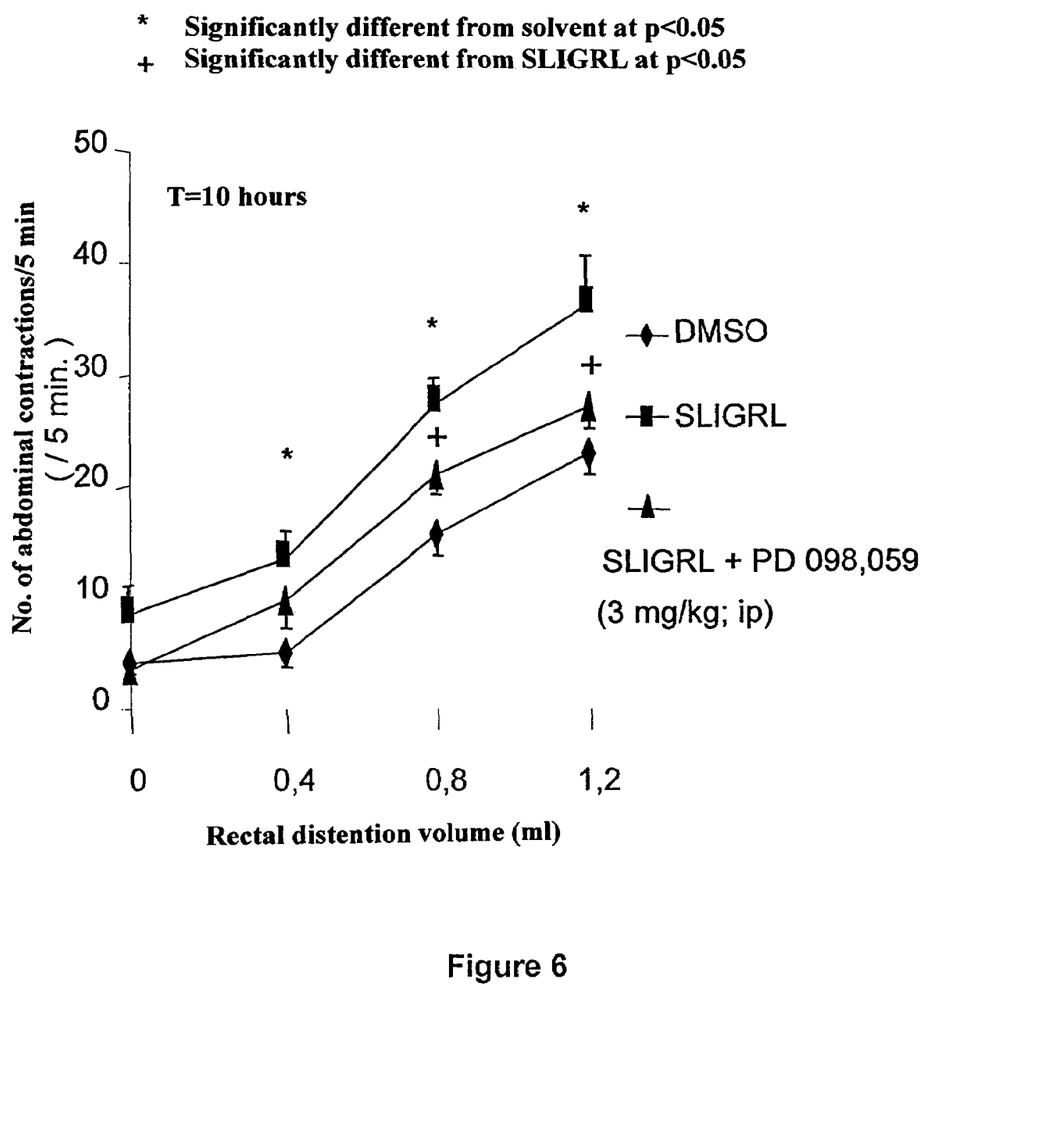
FIG. 6: Effects of repeated administration of an MLCK inhibitor on rectal hyperalgesia induced by intracolonic administration of SLIGRL (200 µg) in rats. With regard to SLIGRL-induced hyperalgesia, only administration of PD 098 059 (one dose of 3 mg/kg) reduced hyperalgesia for all distention volumes.

The protocol described in example 1 was used on 3×3 groups of 7-8 rats given intracolonic infusion of SLIGRL (200 µg) or taurocholate (5 mM) but previously treated with PD 98059. (MEK inhibitor) by the intramuscular route. The results presented in FIG. 6 show that a single treatment with PD 98059 at a dose of 3 mg/kg reduced hyperalgesia induced by intracolonic administration of SLIGRL.

Example 5

Reduction of Stress-Induced Hyperalgesia by ML-7

Figure 11:
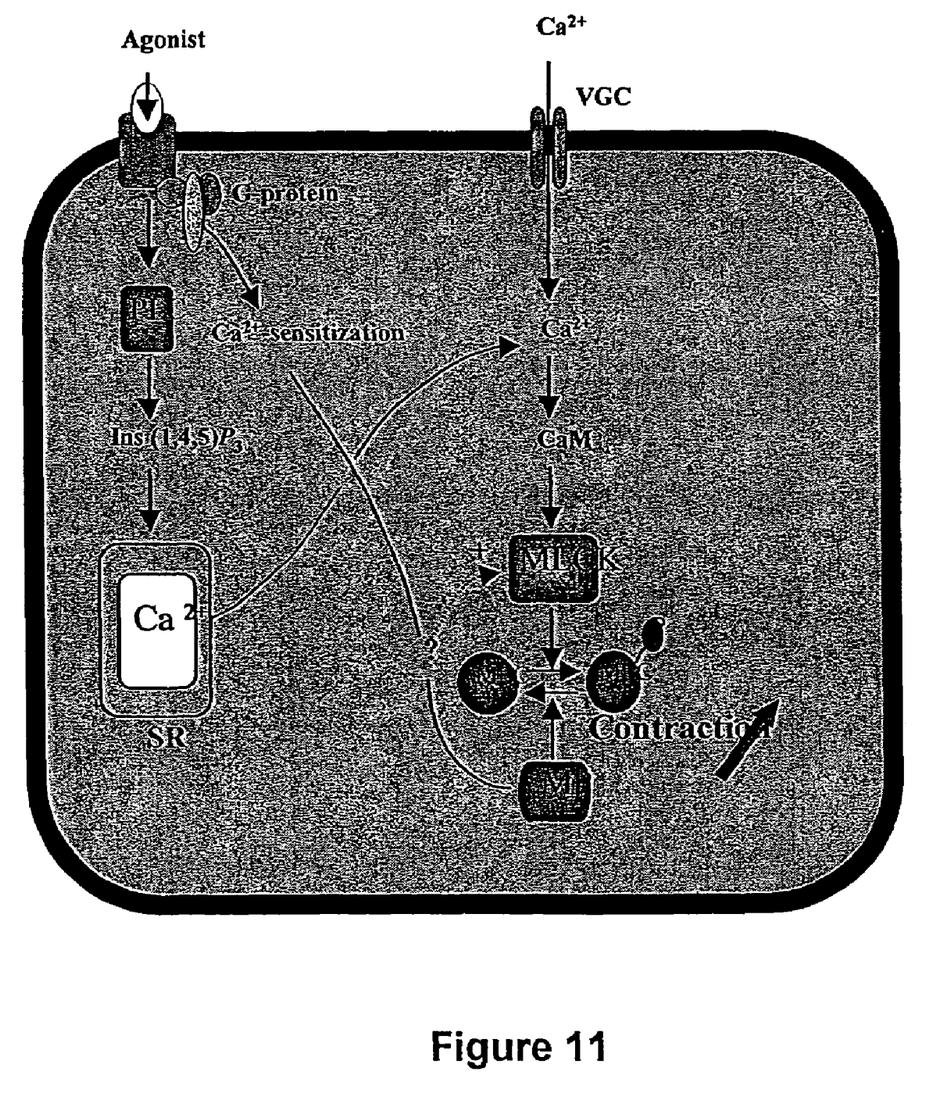
FIG. 11: Myosin light chain kinase (MLCK) and myosin phosphatase (MP) have an opposite action to allow contraction and then relaxation of the myosin light chain of the epithelial cell cytoskeleton (Fukata et al., 2001).
Figure 12:
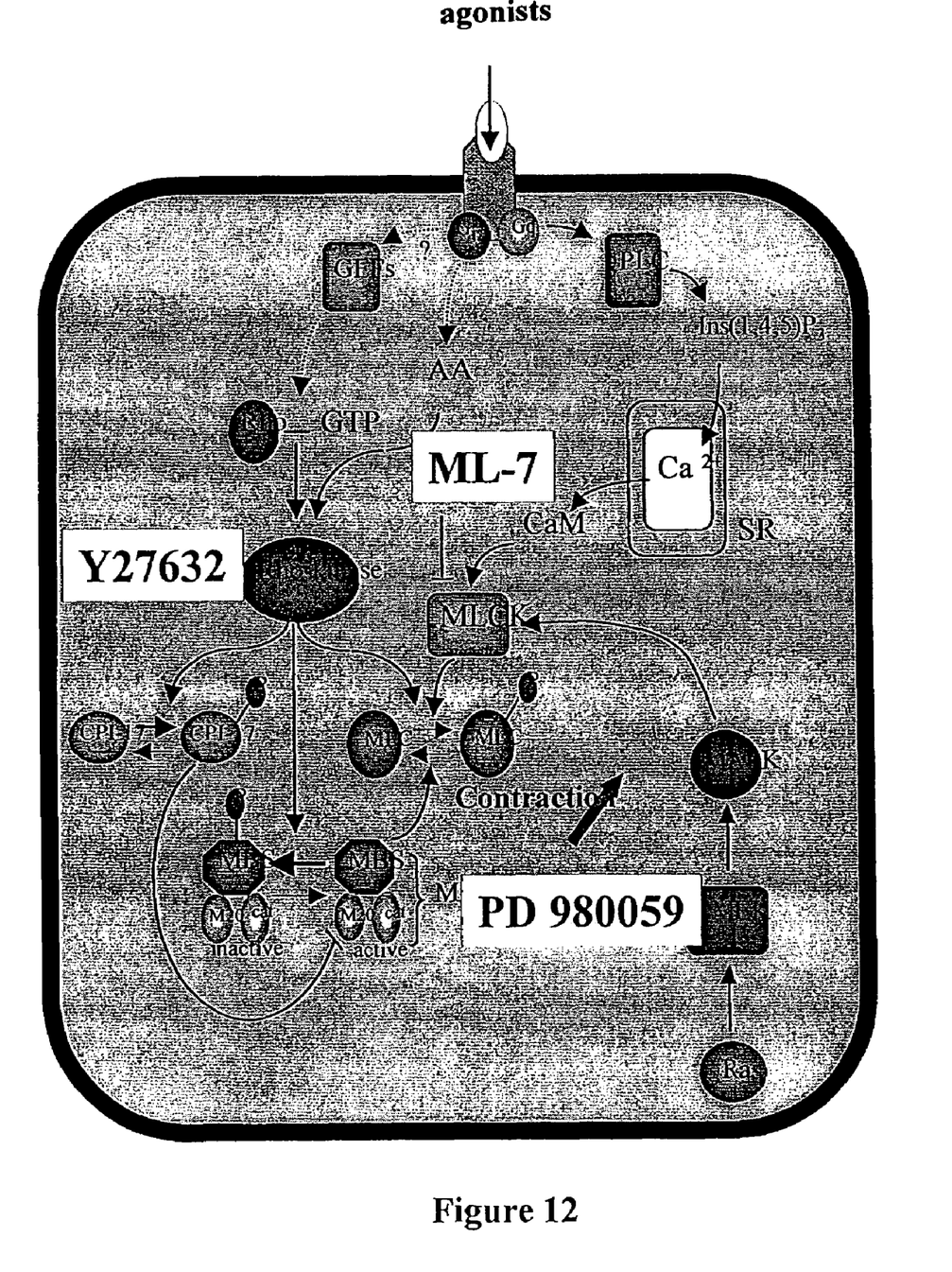
FIG. 12: Molecular targets by which to reduce myosin light chain (MLC) contraction in epithelial cells (Fukata et al., 2001).

Example 2 concerns the effects of a chemical blocker of epithelial tight junctions on stress-induced rectal hyperalgesia. In example 5, the same protocol as in example 2 was used but the animals were treated with an MLCK inhibitor, ML-7, which reduces cytoskeletal contraction. As in the previous example, ML-7 was given as three doses (1 mg/kg i.p.) at 12 hour intervals, over 36 hours prior to stress. The results show that ML-7 inhibited stress-induced hyperalgesia, confirming the interest of targeting the MLCK enzyme for the treatment of colon hypersensitivity in humans (FIG. 11).

The invention claimed is:

1. A method for treating hyperalgesia associated with Irritable Bowel Syndrome comprising administering to a subject in need of such treatment an effective amount of a direct and selective inhibitor of MLCK wherein said inhibitor is 1-(5-iodonaphthalene-1-sulfonyl)-1H-hexahydro-1,4-diazepine.

2. The method of claim 1, wherein the inhibitor is administered by the oral or rectal route.

3. A method for treating hyperalgesia associated with Irritable Bowel Syndrome comprising administering to a subject in need of such treatment an effective amount of a direct and selective inhibitor of MLCK wherein said inhibitor is 1-(5-chloronaphthalene-1-sulfonyl)-1h-hexahydro-1,4-diazepine.

4. The method of claim 3, wherein the inhibitor is administered by the oral or rectal route.

* * * * *